United States Patent [19]

Ofsthun et al.

[11] Patent Number: 5,527,467

[45] Date of Patent: * Jun. 18, 1996

[54] RECTIFYING DIALYZER, BIOREACTOR AND MEMBRANE

[75] Inventors: Norma J. Ofsthun, Rolling Meadows; Lee W. Henderson, Lake Forest; Richard I. Brown, Northbrook; Robin G. Pauley, Ingleside, all of Ill.

[73] Assignee: Baxter International Inc., Deerfield, Ill.

[ * ] Notice: The portion of the term of this patent subsequent to Jan. 10, 2012, has been disclaimed.

[21] Appl. No.: 259,279

[22] Filed: Jun. 13, 1994

Related U.S. Application Data

[63] Continuation of Ser. No. 28,400, Mar. 9, 1993, abandoned, which is a continuation-in-part of Ser. No. 818,851, Jan. 10, 1992, Pat. No. 5,240,614.

[51] Int. Cl.[6] .................................................. B01D 61/28
[52] U.S. Cl. ...................................... 210/645; 210/500.23
[58] Field of Search ............................. 264/41; 210/645, 210/638, 500.23, 500.41

[56] References Cited

U.S. PATENT DOCUMENTS

| | | | |
|---|---|---|---|
| 4,481,260 | 11/1984 | Nohmi | 210/500.23 X |
| 4,804,628 | 2/1989 | Cracauer et al. | 210/500.23 X |
| 5,049,276 | 9/1991 | Saraki | 210/500.23 |
| 5,240,614 | 8/1993 | Ofsthun et al. | 210/500.41 X |

FOREIGN PATENT DOCUMENTS

| | | |
|---|---|---|
| 0201604 | 11/1986 | European Pat. Off. . |
| 0294737 | 12/1988 | European Pat. Off. . |
| WO9006990 | 6/1990 | WIPO . |

OTHER PUBLICATIONS

Patent Abstracts of Japan vol. 12 No. 270 (C–515)[3117] Jul. 27, 1988.

*Primary Examiner*—Frank Spear
*Attorney, Agent, or Firm*—Thomas S. Borecki; Charles R. Mattenson; Robert M. Barrett

[57] ABSTRACT

The invention provides dual-skinned membranes useful as one way or rectifying membranes which reduce back filtration of solute molecules in dialysis and which improve nutrient supply and product recovery in membrane bioreactors. The membranes are dual-skinned polymeric materials preferably in the form of hollow fibers. The membranes have skins of polymer on the opposite sides with differing permeability to solutes and sieving coefficient characteristics. The skin on each side have pores that are invisible at 10,000 times magnification, the microporous structure between said skins contains pores capable of retaining solutes in a molecular weight range of about 5000 to 200000 in an increased concentration between the interior and the exterior skins. Improved dialysis devices are formed by using bundles of the hollow fiber membranes as a dialysis means having rectifying properties.

14 Claims, 6 Drawing Sheets

RECTIFYING DIALYZER, BIOREACTOR AND MEMBRANE

This application is a continuation of application Ser. No. 08/028,400, filed Mar. 9, 1992, and now abandoned, which is a continuation in part of application Ser. No. 07/818,851, filed Jan. 10, 1992, now U.S. Pat. No. 5,240,614.

FIELD OF THE INVENTION

This invention relates to fluid filtration devices, such as blood dialysis devices and bioreactors and membranes for such devices. More specifically, the invention relates to an improved dialysis device having rectifying filtration properties, dual-skinned membranes for performance of such dialysis and other filtration procedures.

BACKGROUND OF THE INVENTION

Dialysis membranes and devices perform important life sustaining functions when used in artificial kidneys and other types of filtration devices. A well recognized problem of high flux dialyzers is the back filtration from dialysate to the blood of undesirable molecules. Due to the high cost of using sterile, pyrogen-free dialysates, it would be highly desirable to have available a dialysis membrane which could remove relatively large solutes such as $\beta$-2microglobulin while preventing passage of similarly sized molecules from dialysate to blood. Membranes, however, which offer a high rate of diffusion of solutes from the blood to dialysate also suffer from high rates of back diffusion of solutes from dialysate back to the blood. Similarly, existing membranes which offer a high rate of convection also suffer from high rates of back filtration. A need has therefore existed for dialysis membranes which provide for adequate removal of uremic toxins from the blood while preventing back transport of undesirable substances to the blood. Similarly, other fluid filtration processes benefit from the availability of membranes having such rectifying properties.

A need has also existed for devices such as bioreactors in which rectifying membranes provide a means for simultaneously supplying nutrients to and carrying products and waste byproducts from live cells that are used to make products which cannot be economically produced by traditional synthetic chemistry techniques.

SUMMARY OF THE INVENTION

An important object of the invention is to provide new and improved membranes for filtration devices such as dialysis devices. A further aspect of the invention is to provide improved filtration devices containing membranes with rectifying properties, i.e., have a greater sieving coefficient in one direction than the other, and improved filtration methods using such devices.

A further important aspect of the present invention involves providing dual-skinned membranes such as hollow fibers in which the pore size and structure, and the resulting sieving coefficient, differs between the two opposed surfaces of the membrane. In the preferred embodiment, the membranes are in the shape of hollow fibers in which the sieving coefficient, or permeability to molecules of a particular size, of the inner wall or skin of the fiber is greater than that of the outer wall. Such fibers can be assembled into dialysis devices in accordance with known procedures to provide such dialysis devices in which large solutes can be removed from a fluid, such as blood, flowing within the interior of the fibers to a filtrate or dialysate liquid which surrounds the fibers. Since a tighter or less permeable skin is provided on the outside of the fibers, it has been found that back transport from the outside of the fibers to the inside is substantially reduced.

Another important object of the invention is to provide dual-skinned membranes useful in dialysis as one way or rectifying membranes which reduce back filtration. The preferred membranes are dual-skinned polymeric materials preferably in the form of hollow fibers. The membranes have skins of polymer on their opposite sides with differing solute permeability or sieving coefficient characteristics. Such membranes can be formed by extruding a polymer dissolved in a solvent while contacting at least one surface with a non-solvent for the polymer that is miscible with the solvent. The other surface is also contacted with a non-solvent, but one which is either different from the first non-solvent or which contains a soluble additive that changes the pore size and structure of the skin formed on the dissolved extruded polymer.

In another aspect of the invention improved dialysis devices having rectifying properties are formed by using the membranes provided by the invention. The preferred dialysis devices of the invention are formed from hollow polymeric fiber membranes having a microporous structure within the walls thereof, with the microporous structure having a skin of polymer containing invisible pores formed integrally with the interior and exterior surfaces thereof. The exterior skin has a sieving coefficient different from that of the internal skin. The rectifying dialysis devices of the invention provide a means for removing unwanted material from bodily fluids such as blood in which a high rate of filtration of solutes from blood to dialysate is offered, while a substantially lower rate of back filtration of undesired solutes from dialysate to blood is maintained.

DRAWINGS

The invention will be further explained in the following detailed description and with reference to the accompanying drawings, wherein.

DETAILED DESCRIPTION

Figure 1:
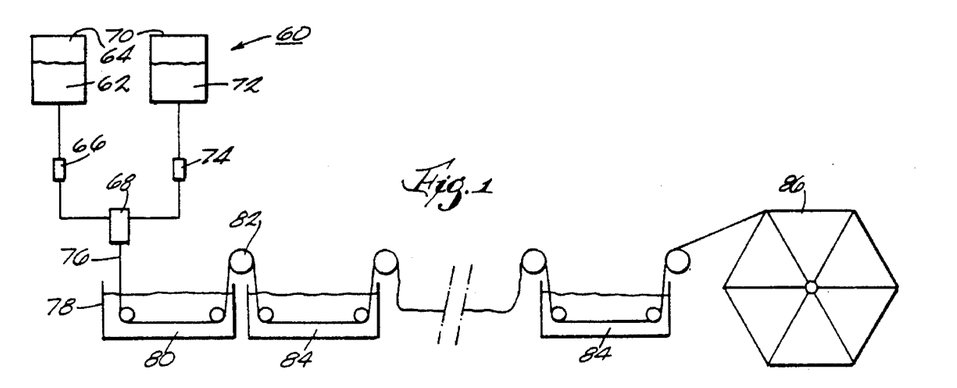
FIG. 1 is a diagrammatic view illustrating the process for forming membranes of the invention in hollow fiber form.

Referring more specifically to the drawings, FIG. 1 diagrammatically illustrates a hollow fiber spinning system 60. A solution 62 of a polymer in an organic solvent is contained in vessel 64 from where it is pumped to an annular extrusion die 68 by means of a metering pump 66. Similarly, a coagulant solution 72 which is a non-solvent for the polymer is contained in a second vessel 70 and is transferred to die 68 by means of another pump 74.

The interaction of non-solvent 72 and the polymer solution 62 at the interface 63 formed as the solutions exit the die in contact with each other determined the ultimate structure and properties of the inner membrane.

Figure 3:
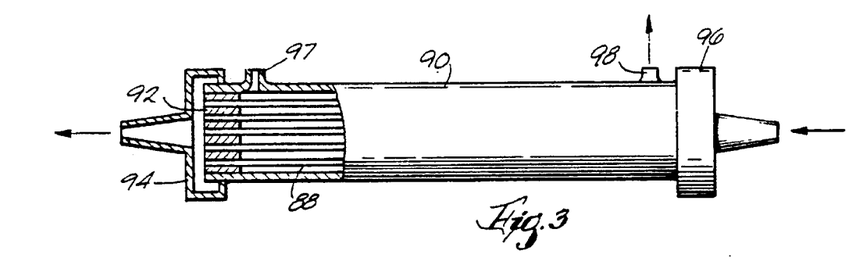
FIG. 3 is a side elevational view with portions in cross-section of a filtration device of the present invention.

The formed extrudate then falls through an air gap 76 and enters a bath 78 containing a second non-solvent coagulant solution 80. The interaction of the extrudate with the second solution 80 determines the structure and properties of the outer membrane. The fiber is pulled through bath 78 by means of driver roller 82 and through one or more additional baths 84, as required, to completely extract the solvent from hollow fibers. The extracted fiber is finally taken up onto a multi-segment winder 86 and allowed to dry. Dried fibers 88 are cut to length and placed in a housing 90. The fibers 88 are sealed in the housing by means of a thermosetting resin 92. The assembly is fitted with end caps 94 and 96. An inlet 97 and outlet 98 for filtrate liquid are also provided on the housing.

Figure 5:
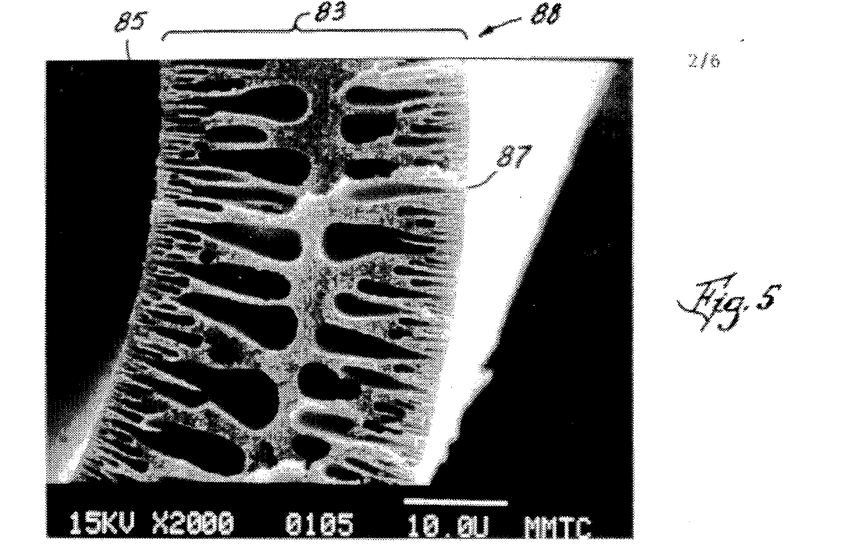
FIGS. 5 and 6 are cross-sectional views of a hollow fiber membrane of the invention of different magnifications taken with an electron microscope; and, FIG. 7 is a side elevational view of a bioreactor device in accordance with the invention.
Figure 6:
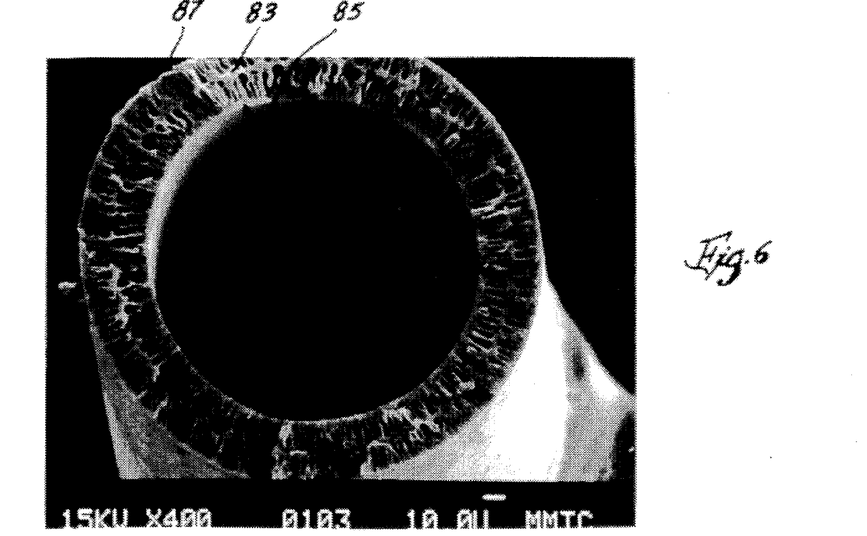

FIGS. 5 and 6 illustrate in magnified cross-section a typical fiber 88 of the invention showing internal microporous structure 83, an inner skin 85 and an outer skin 87 having different porosity than inner skin 85. Membranes of this invention preferably have an inner diameter of about 200 microns and generally range in inner diameter from about 100 to 1000 microns.

The overall sieving coefficient is the fraction of the incoming solute that passes through the membrane along with the fluid that is being filtered. It is calculated by dividing the concentration of solute on the downstream side of the membrane by its concentration on the upstream side of the membrane.

For a single-skinned membrane, the overall sieving coefficient is equal to the sieving coefficient of the skin, which is the fraction of solute that passes through that skin. The sieving coefficient of the skin itself depends only on the relative sizes of the pore and the solute molecule. The tighter the skin (i.e. smaller the pores), the smaller the fraction of a given molecule which will pass through it.

However, for a dual-skinned membrane, the concentration of solute which reaches the second skin depends on the characteristics of the first skin as well as the flow conditions, so the overall sieving coefficient is a property of both flow and membrane properties. The key to the rectifying membrane, in which the sieving coefficient in one direction is different from the sieving coefficient in the other direction, is that flow in one direction results in buildup of solute within the two skins of the membrane.

Figures 2, 4:
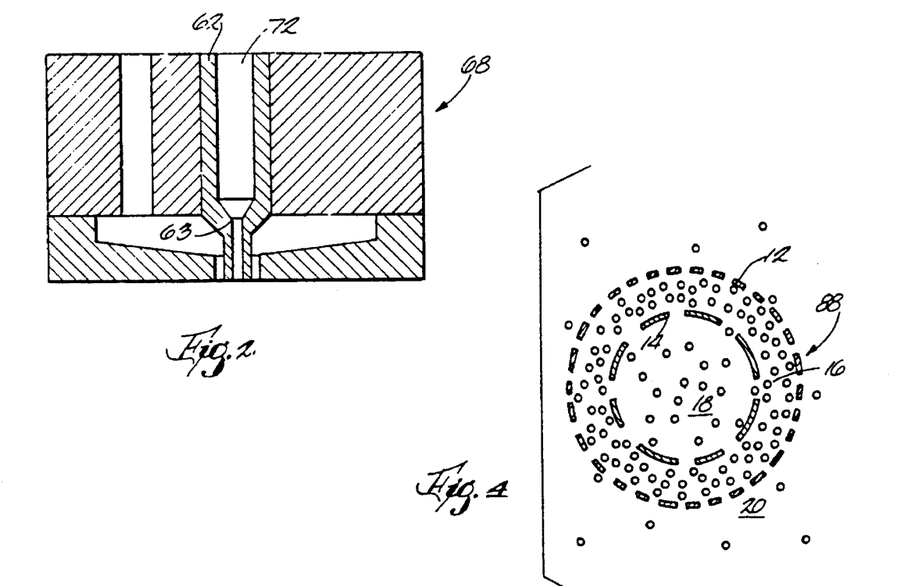
FIG. 2 is a cross-sectional view of an annular extrusion die used in the practice of the invention.
FIG. 4 is a sketch in greatly enlarged scale illustrating, hypothetically, the mechanism of filtration that occurs in use of the filtration devices of the invention.

FIG. 4 is a schematic of a dual-skinned rectifying membrane 88 in which the outer skin 12 is tighter than the inside skin 14 and fluid is passing from the inside to the outside as a result of an imposed pressure gradient. In this case, some of the molecules which enter the central area 16 of membrane 88 become trapped when they reach the tighter outer skin 12. The concentration inside the membrane goes up until it reaches a steady state value, and the resulting concentration in the fluid 20 outside the fiber goes up along with it. The concentration in the fiber lumen 18 has not changed, so the overall sieving coefficient increases with time until it reaches a steady-state value that is higher than would be obtained with the tight skin 12 alone.

If that same membrane is exposed to a pressure gradient from the opposite direction, with flow from the outside to the inside, the solute has a hard time getting into the membrane at all, so there is no buildup in the membrane. In this case both the concentration within the membrane and the concentration on the downstream side of the membrane are low, and the overall sieving coefficient is smaller than that which was obtained in the other direction.

Various polymers can be employed in the process of the invention to form hollow fibers. The polymers must be soluble in at least one organic solvent and insoluble in another liquid that is miscible with the solvent. Examples of suitable polymers are polysulfone, polyetherimide, polyacrylonitrile, polyamide, polyvinylidene diflouride, polypropylene, and polyethersulfone. Illustrative examples of solvents for such polymers include N-methyl-2-pyrrolidone, N,N'-dimethylformamide, N,N'-dimethylacetamide and γbutyrolactone. The preferred non-solvent which can be used as a coagulation or gelation agent for formation of the skins is water. Other suitable liquids include methanol, ethanol-water mixtures such as 95 or 99.5 vol % ethanol in water, or isopropyl alcohol. Various materials can be added to the non-solvents to form skins of differing porosities. Examples include polyvinyl alcohol, Tetra-ethylene-glycol, poly-ethylene-glycol, perchlorate salts, and polyvinyl pyrrolidone.

An important advantage of the present invention is the ability to provide fibers having different sieving coefficients depending on the direction of filtrate flow, for molecules to be filtered out of a liquid. A further advantage is the ability to provide fibers having different sieving coefficients for filtration out of a liquid of molecules having narrowly defined molecular weight ranges. For example, fibers can be provided that have the ability to filter molecules in the range of 5000 to 10,000 differently from one side of the membrane than the other. By appropriate modification of the porosity, the sieving coefficient differential can also be optimized for molecules having a molecular weight range of 10,000 to 100,000 or even 200,000. Optimization is achieved by adjusting the composition of the coagulant solution and the amount and type of dopants added, as well as by varying the spinning conditions such as flow rate, line speed and gap distance.

EXAMPLES

The following examples illustrate preferred processes for producing and using membranes in accordance with the invention. All parts are given by weight unless otherwise indicated.

EXAMPLE 1

Hollow fibers were prepared using the spinning system and processes described in FIGS. 1 and 2 under the formulation and process conditions shown in Table I.

Test Procedure

Test modules were assembled by potting 100 fibers in mini-dialyzer cases with a length of about 22 cm and an internal diameter of about 0.6 cm. Polyurethane potting extended approximately 1 cm from each header, leaving an active length of about 20 cm. Dialysate ports were located approximately 1 cm from the potting material at each end.

Standard dialysate of the following composition was prepared from concentrate using a hemodialysis machine proportioning system:

sodium 134 mEq/l potassium 2.6 mEq/l calcium 2.5 mEq/l magnesium 1.5 mEq/l chloride 104 mEq/l acetate 36.6 mEq/l dextrose 2500 mEq/l Myoglobin solution was prepared by adding the 330 mg of myoglobin per liter of dialysate. Myoglobin (molecular weight=17,000) is used as a marker for middle molecules such as B-2 microglobulin (molecular weight=12,000) because it can be measured spectrophotometrically.

The lumen and filtrate compartments were primed with alcohol (isopropanol or ethanol) using a syringe. The test module was then rinsed with excess dialysate, pumping 250 ml through lumen with filtrate port closed and then 200 ml more with one filtrate port open. To measure inlet flow rate, the dialysate ports were closed, the infusion pump was set to the desired speed (10.5 ml/min), outflow was determined by timed collection.

For the sieving coefficient measurement, the test module was clamped in a vertical position, with fibers perpendicular to the table top. An infusion pump was connected to an inlet reservoir, and tubing from the infusion pump was connected to the bottom header. Tubing to waste was connected to the top header. The dialysate ports were closed, the pump was started, and the time at which the test solution reached the device was denoted as time zero.

At time zero, the dialysate side was drained of priming solution by opening both dialysate stopcocks. The lower dialysate port was then closed, and the time zero filtrate sample was taken from the upper port as soon as the filtrate compartment was filled. At the same time, the outlet lumen sample was collected into another beaker. Inlet lumen samples were taken directly from the inlet reservoir. Subsequent filtrate samples were collected at 3 minute intervals, with no loss of filtrate between samples. All samples were measured for myoglobin content using a Gilford spectrophotometer. The sieving coefficient, S, was calculated using the following equation:

$$S = \frac{2 \times \text{concentrate in dialysate}}{(\text{inlet lumen concentration} + \text{outlet lumen concentration})}$$

Sampling was continued until the calculated sieving coefficient was constant for 3 consecutive samples.

The fibers were assembled into test modules and the sieving coefficients determined in accordance with the foregoing procedure. The sieving coefficients of the fibers of this example for myoglobin were found to be 0.35 when filtrate flow was directed radially outwardly and 0.80 when filtrate flow was inward.

TABLE I

| | |
|---|---|
| Polymer | Polysulfone |
| Solvent | N-methylpyrrolidone |
| Spinning Solution Concentration | 15 g/100 g |
| Core Fluid Composition | 15/85 2-propanol/water |
| Precipitation Bath Composition | 2/98 2-propanol/water |
| Wash Baths Composition | Water |
| Gap Distance | 1 cm |
| Line Speed | 18 meters/min |
| Spinning Solution Flow Rate | 1.8 cc/min |
| Core Fluid Pin Diameter | 0.009 inches |
| Die Annular Gap | 0.0035 inches |

EXAMPLE 2

Hollow fibers were prepared as in Example 1 except that the core fluid composition was 10/90 2-propanol/water and that of the precipitation bath was 5/95 2-propanol/water. FIGS. 5 and 6 are scanning electron micrographs of the resulting fiber in cross-section taken at 2000 times magnification and 400 times magnification, respectively, showing the finger-like structures extending from each boundary and meeting in the middle wall. Sieving coefficients for myoglobin were found to be 0.45 for outward filtrate and 0.90 for inward flow.

EXAMPLE 3

Hollow fibers were prepared as in Example 1 except that the core fluid composition was 70% isopropyl alcohol and 30% water. The spinning solution concentration was 20 weight percent of polysulfone in N-methylpyrrolidone with 10% acetone. The precipitation bath was water. Sieving coefficients were determined for dextran using the following procedure:

1) Dextran Sieving Coefficient. A dextran solution of the following composition was prepared in phosphate buffered saline (0.9%):

Dextran FP1 (Serva) 0.2 g/l

Dextran 4 (Serva) 1.0 g/l

Dextran T40 (Pharmacia) 1.0 g/l

Dextran T10 (Pharmacia) 0.3 g/l

Dextran solution was perfused through the lumen, with filtrate collected from the shell side. Dextran solution was also perfused through the shell side, with filtrate collected from the lumen. The order of the tests varied. Solution flow rate was 5 ml/min, and the transmembrane pressure was between 150 and 200 mm Hg. Inlet samples were taken directly from the dextran solution reservoir. Filtrate samples were taken at 5 minutes intervals. The filtrate concentration values stabilized after 15 minutes. The filtrate concentration value at 40 or 60 minutes were used to calculate sieving coefficient. The bulk solution concentration was assumed to be equal to its inlet value and constant throughout the length of the dialyzer. Samples were analyzed by high performance liquid chromatography (HPLC) using a refractive index detector.

$$S = \frac{\text{filtrate concentration}}{\text{bulk concentration}}$$

Figure 8:
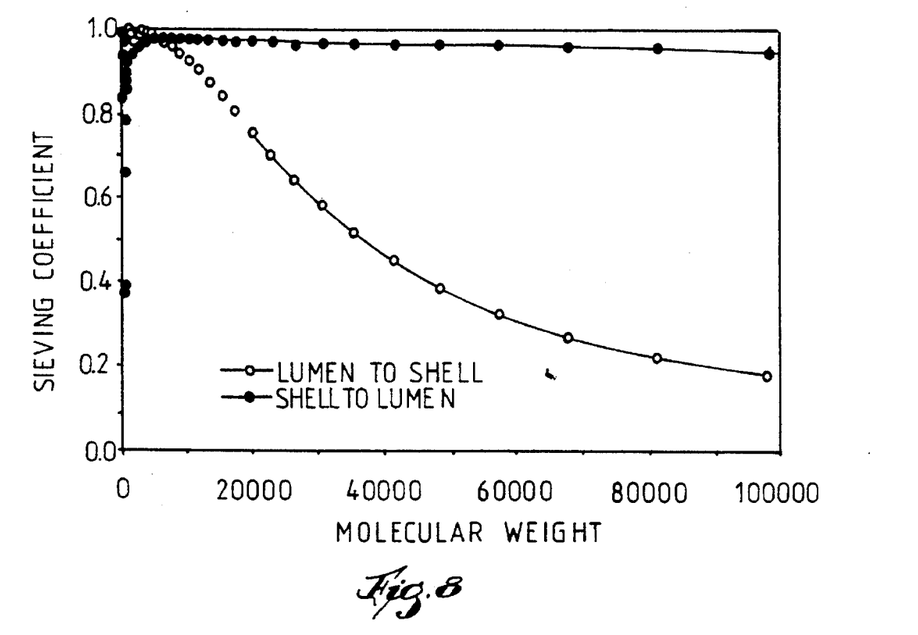
FIGS. 8–14 are graphical representations of the results obtained from testing of specific examples described herein.

Results are shown in FIG. 8.

Sieving coefficients for alcohol dehydrogenase (MW approximately 150,000) and β-amylase (MW approximately 200,000) were determined by the procedure outlined above, by with the samples analyzed by a commercially available assay kit (Sigma Chemical Co.). The sieving coefficients for alcohol dehydrogenase were 0.05 for outward flow and 0.76 for inward flow. The sieving coefficients for β-amylase were 0.01 for outward flow and 0.17 for inward flow.

EXAMPLE 4

Figure 9:
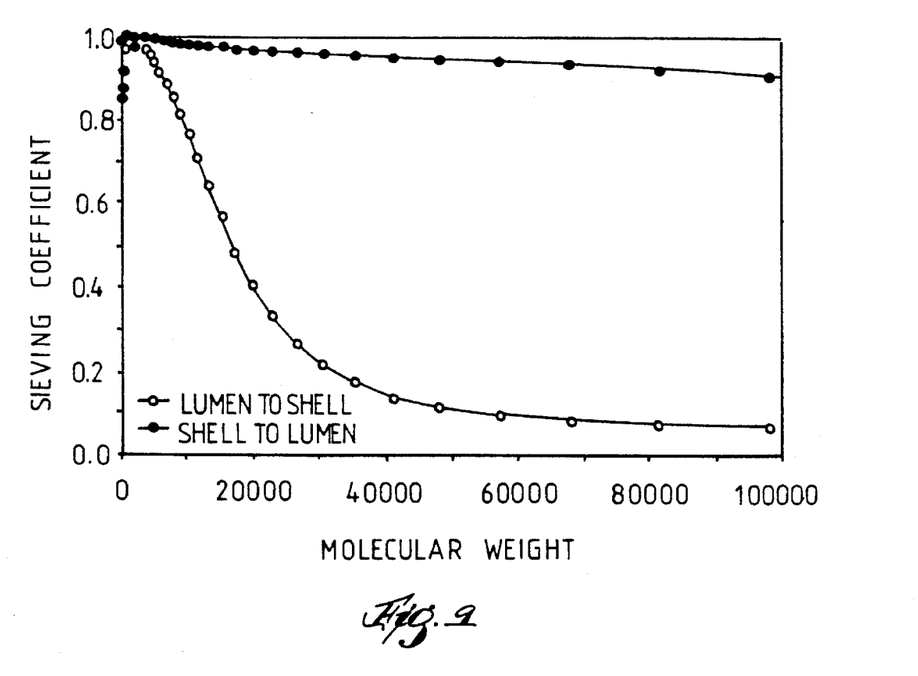

Hollow fibers were prepared as in Example 1 except that the core fluid composition was 50% isopropyl alcohol and 50% water. The spinning solution contained 20% by weight of polysulfone and N-methylpyrrolidone with 10% acetone. The precipitation bath was water. The sieving coefficient for dextran was determined for lumen to shell and shell to lumen. The results are shown in FIG. 9.

EXAMPLE 5

Figure 10:
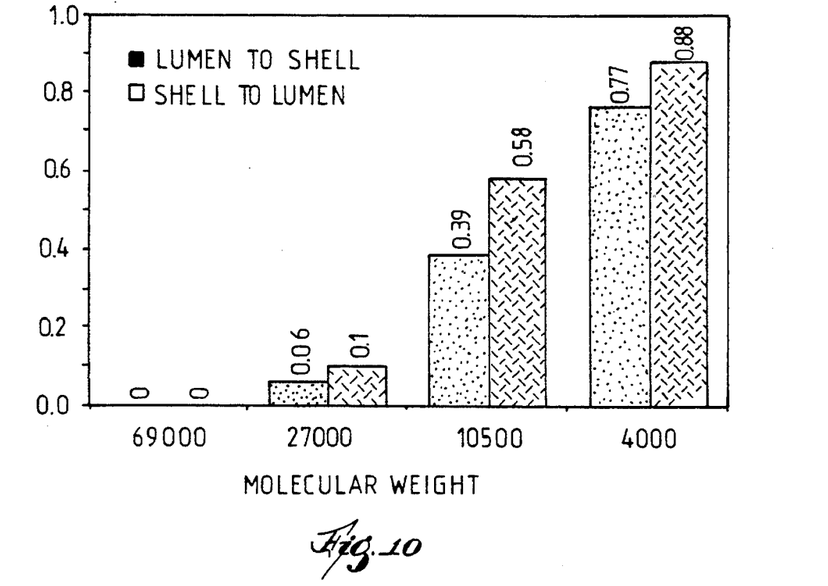

Hollow fibers were prepared as in Example 1 except that the core fluid composition was isopropyl alcohol. The spinning solution was polysulfone in a concentration of 15% by weight and in addition 15% by weight of polyvinylpyrrolidone in N-methylpyrrolidone. The core fluid composition was isopropyl alcohol and the precipitation bath was water. The sieving coefficient for dextran was determined as in Example 3 with the results being shown in FIG. 10.

EXAMPLE 6

Polysulfone hollow fiber membranes were prepared with an outer skin having a 5,000 kilodalton (kD) nominal molecular weight (MW) cutoff and a skin with a larger, but unknown MW cutoff on the inner fiber surface. For these fibers, the sieving coefficients of dextrans of various molecular weight were found to be greater when filtrate flow was directed radially inward than when filtrate flow was directed outward.

Protein Sieving Coefficient. The following proteins were dissolved in phosphate buffered saline (0.9%):

| | |
|---|---|
| Solution 1 | 2.0 g/l |
| Bovine serum albumin | |
| Solution 2 | 1.0 g/l |
| Ovalbumin (chicken egg albumin) | |
| Solution 3 | 0.08 g/l |
| Myoglobin | |
| Solution 4 | 0.12 g/l |
| Cytochrome c | |

Figure 11:
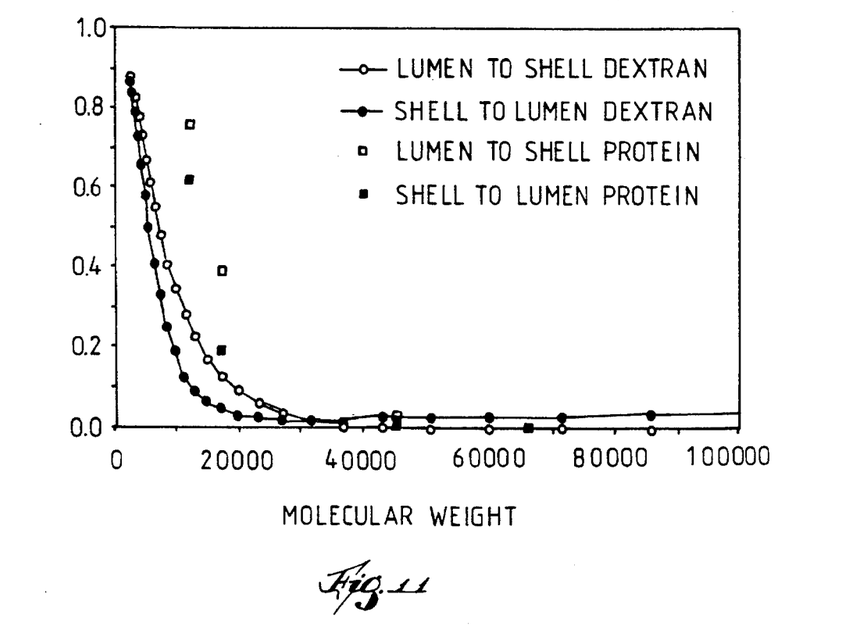

Protein solution was perfused through the lumen, with filtrate collected from the shell side. Protein solution was also perfused through the shell side, with filtrate collected from the lumen. The order of the tests varied. Inlet samples were taken directly from the protein solution reservoir. Filtrate samples were taken at 5 minutes intervals. The filtrate concentration values stabilized after 15 minutes. The filtrate concentration value at 40 or 60 minutes were used to calculate sieving coefficient. The bulk solution concentration was assumed to be equal to its inlet value and constant throughout the length of the dialyzer. Samples were analyzed for absorbance at a characteristic wavelength using a spectrophotometer. Bovine serum albumin and ovalbumin were analyzed at 280 nm. Myoglobin and cytochrome c were analyzed at 410 nm. The results for sieving coefficients of both dextran and proteins tested according to the foregoing procedure are shown in FIG. 11.

EXAMPLE 7

Hollow fibers were prepared according to the procedure of Example 1 using the following materials:

Polymer: Polyetherimide

Solvent: N-methylpyrrolidone

Spinning solution concentration: 20 wt %

Core fluid composition: Water

Precipitation bath: Water

Figure 12:
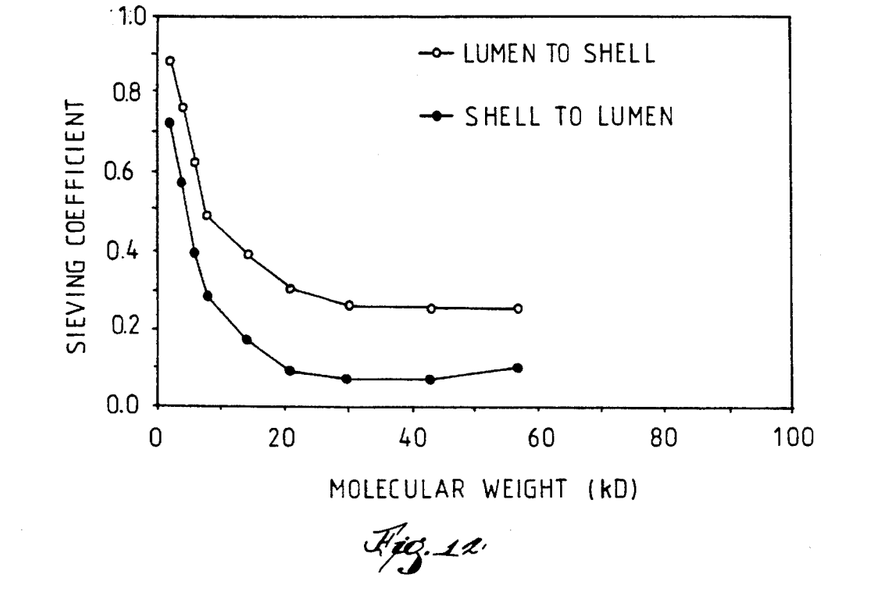

The sieving coefficient data for dextran when tested as shown in FIG. 12.

EXAMPLE 8

Hollow fibers were prepared according to the procedure of Example 1 using the following materials:

Polymer: Polyetherimide

Solvent: N-methylpyrrolidone

Spinning solution concentration: 25 wt %

Core fluid composition: 50/50 Water/N-methylpyrrolidone

Precipitation bath: Water

Figure 13:
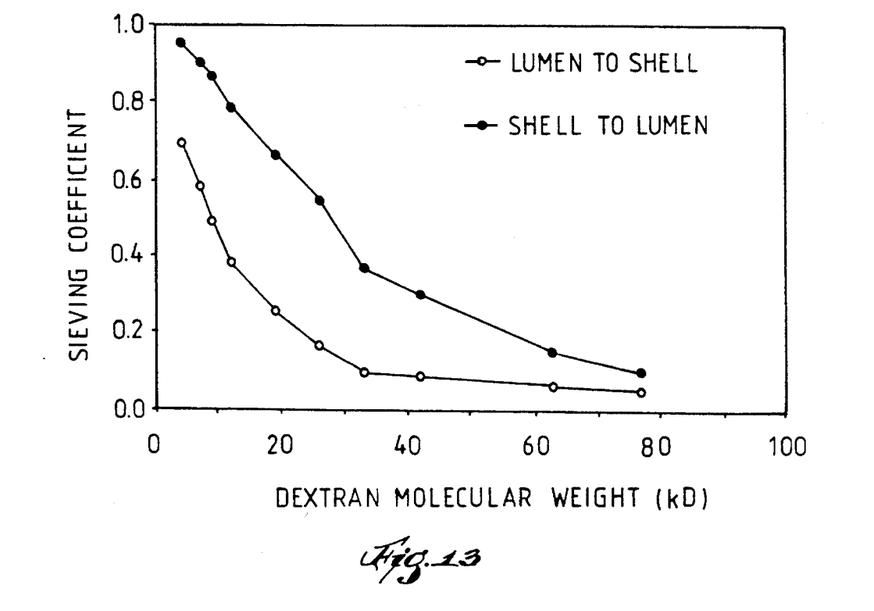

The sieving coefficient data for dextran is shown in the following FIG. 13.

EXAMPLE 9

According to current theory on the behavior of rectifying membranes, internal concentration polarization of solute is responsible for the asymmetric sieving characteristics of the above examples. The accumulation of solute between the two skins of the membrane should require a finite amount of time to occur. Consequently, the sieving coefficient in one direction should increase with time until equilibrium is reached. For most common membranes, the sieving coefficient is generally greatest in early time measurements and may decrease with time as pores clog with retained solute.

Figure 14:
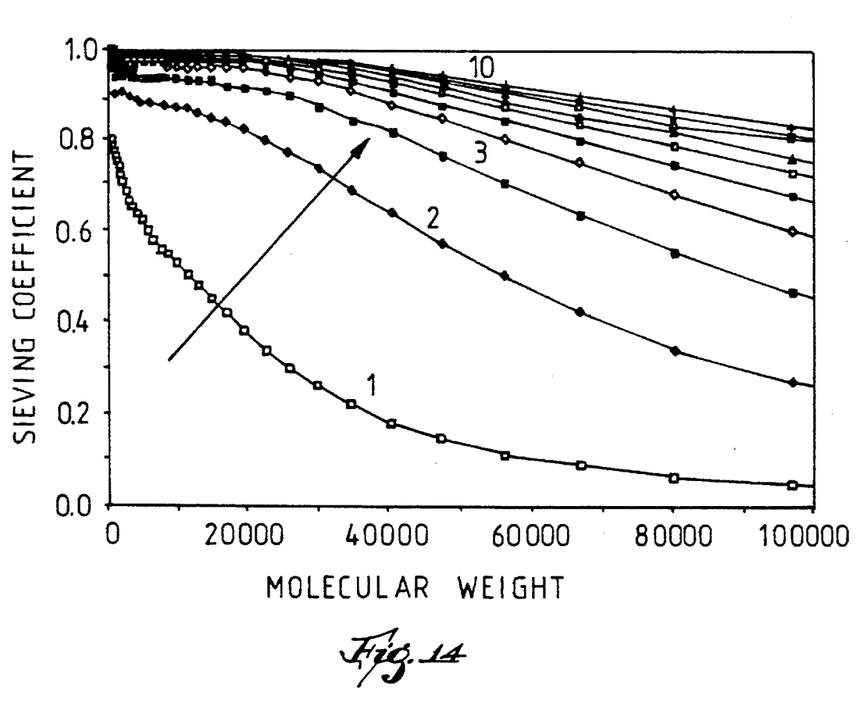

In FIG. 14, the sieving coefficient in the shell to lumen direction is shown as a function of time for the membrane of Example 3. For this experiment, filtrate was collected at one minute intervals for the first ten minutes of filtration. The sieving coefficient, particularly in the 50,000 to 100,000 range, did increase significantly with time.

Figure 7:
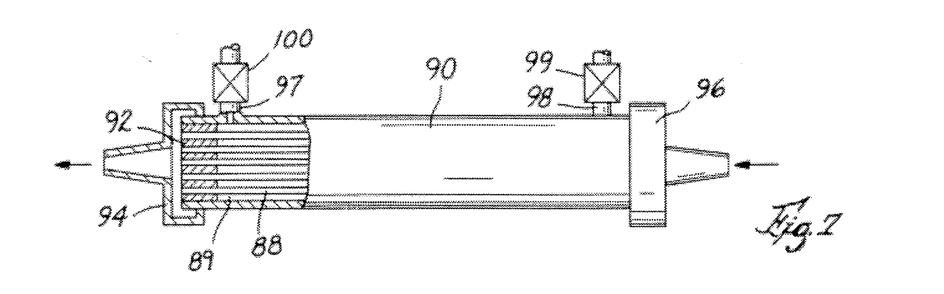

A bioreactor is shown in FIG. 7 and consists of a device somewhat similar to the dialysis device shown in FIG. 3. In this case, however, the space 89 surrounding the fibers and enclosed by the interior of housing 90 and thermosetting resin 92 forms a reaction vessel for growth of living cells. Ports 97 and 98 are either omitted or can be closed by means of valves 99 and 100 as indicated. Depending on its size, the product may pass back through the membranes 88 and be purified from the waste stream or it may collect in the shell space which constitutes the reaction vessel from which it may be removed on either a semi-continuous or batch basis.

Transport of nutrients, waste products and desired biological products across the membrane may be by diffusion and/or convection. The axial pressure drop which occurs within the hollow fibers leads to Starling's flow, with convection from the tube side to the shell side at the device inlet and convection from the shell side to the tube side at the device outlet.

Some types of cells require expensive growth media which may contain 10% bovine fetal calf serum. Use of a rectifying membrane allows serum components to pass through the membranes to the cells and then be concentrated in the shell space, thereby reducing the volume of media required. This also reduces the cost of purifying products which pass through the membrane because the volume of the purification stream is smaller.

Rectifying membranes can also be used to concentrate products directly. If the desired product is formed of molecules that are larger than the metabolic waste products as well as the nutrients, the rectifying membrane device can be used to concentrate the products in the shell space while allowing nutrients to reach the cells and waste products to be washed away by the fluid stream passing through the interiors of the hollow fiber membranes.

Membranes in accordance with the present invention can thus be formed with the tighter skin either on the interior or exterior of a hollow membrane. In either event it is important that the skins on each side of the membrane contain pores that are invisible at 10,000 times magnification. This will insure the presence of sufficiently tight skins on each side of the membrane to cause a build-up of solutes in the microporous interior of the membrane between the skins. Such build-up of solutes is believed to be important to the construction of membranes in which different sieving coefficients are obtained for flow through the membrane in different directions.

What is claimed is:

1. A bioreactor comprising a plurality of dual-skinned hollow polymeric membranes having a microporous structure between walls thereof, said microporous structure having a skin of polymer formed integrally with the interior an exterior surfaces thereof, the microporous structure containing pores capable of retaining solutes of a selected molecular weight range within a molecular weight range of about 5000 to 200000 in an increased concentration between the interior and exterior skins, each of said skins having micropores invisible at 10,000 times magnification, the membrane having an overall sieving coefficient for passage therethrough in one direction of fluids containing solutes comprising molecules in said selected molecular weight range different from the overall sieving coefficient for passage of such fluids in the opposite direction, said hollow polymeric membranes being secured in a generally parallel orientation in an enclosure, the opposite ends of said enclosure being formed by a polymeric resin which envelopes the exteriors of said fibers, the opposite ends of said fibers extending through said polymeric resin, the exteriors of said fibers and the interior of said enclosure defining a bioreaction vessel for the growth of living cells, inflow means for a fluid which is in fluid flow communication with the interiors of said membranes, outflow means in fluid communication with the other ends of said membranes for outflow of said fluid, an opening, normally closed, for introduction and removal of fluids from the interior of said vessel.

2. A method of producing biological products comprising confining living cells in a bioreactor vessel comprising a plurality of dual-skinned hollow polymeric membranes having a microporous structure between the walls thereof, said microporous structure having a skin of polymer formed integrally with the interior and exterior surfaces thereof, the microporous structure containing pores capable of retaining solutes of a selected molecular weight range within a molecular weight range of about 5000 to 200000 in an increased concentration between the interior and exterior skins, each of said skins having micropores invisible at 10,000 times magnification, the membrane having an overall sieving coefficient for passage therethrough in one direction of fluids containing solutes comprising molecules in said selected molecular weight range different from the overall sieving coefficient for passage of such fluids in the opposite direction, said hollow polymeric membranes being secured in a generally parallel orientation in an enclosure, the opposite ends of said enclosure being formed by a polymeric resin which envelopes the exteriors of said fibers, the opposite ends of said fibers extending through said polymeric resin, the exteriors of said fibers and the interior of said enclosure defining a bioreaction vessel for the growth of living cells, inflow means for a fluid which is in fluid flow communication with the interiors of said membranes, outflow means in fluid flow communication with the other ends of said membranes for outflow of said fluid, an opening, normally closed, for introduction and removal of fluids from the interior of said vessel, causing a fluid containing nutrients for said cells to flow through said hollow membranes to allow transport of said nutrients through said membrane to said cells, removing waste materials from said cells as they are transferred through said membrane to said fluid, and, subsequently, removing a biological product from said vessel.

3. A dual-skinned hollow polymeric membrane having a microporous structure within the walls thereof, said microporous structure having a skin of polymer formed integrally with the interior and exterior surfaces thereof, the skin on each of said surfaces having pores invisible at 10000 times magnification, the microporous structure between said skins containing pores capable of retaining solutes of a selected molecular weight range within a molecular weight range of about 5000 to 200,000 in an increased concentration between the interior and the exterior skins, the membrane having an overall sieving coefficient for passage of fluids containing solutes comprising molecules in said selected molecular weight range in one direction different from the overall sieving coefficient for such fluids passing therethrough in the opposite direction.

4. A membrane according to claim 3 comprising a hollow polysulfone fiber.

5. A membrane according to claim 3 wherein the skin on the inner surface of said hollow membrane is less restrictive to passage of such solutes than the skin on the outer surface.

6. A membrane according to claim 3 wherein the skin on the outer surface of said hollow membrane is less restrictive to passage of such solutes than the skin on the inner surface.

7. A membrane according to claim 3 comprising a hollow polyetherimide fiber.

8. A membrane according to claim 5 having an inner diameter of about 100 to 1000 microns.

9. A dual-skinned hollow polymeric membrane having a microporous structure within the walls thereof, said microporous structure having a skin of polymer formed integrally with the interior and exterior surfaces thereof, each of said skins having pores invisible at 10,000 times magnification of a size and structure capable of permitting migration therethrough of solute molecules of a selected molecular weight range within a molecular weight range of about 5000 to 200,000, but sufficiently restrictive to such migration to cause an increase in concentration of such molecules in said microporous structure, when a liquid containing such solutes is filtered through said membrane from the side having the looser of said skins toward the side having the tighter of said skins, the overall sieving coefficient of said membrane for passage of fluids containing solutes comprising molecules in said selected molecular weight range in one direction is different than for such fluid passing therethrough in the opposite direction.

10. A membrane according to claim 9 wherein said membrane comprises a polysulfone polymer.

11. A membrane according to claim 10 in which one of said skins has a different sieving coefficient for molecules of a molecular weight of about 10,000 to 20,000 than that of the other of said skins.

12. A device for filtration of fluids comprising a plurality of dual-skinned hollow polymeric membranes secured in a generally parallel orientation in an enclosure, said dual-skinned hollow polymeric membranes having a microporous structure within the walls thereof, said microporous structure having skins of polymer formed integrally with the interior and exterior surfaces thereof, each of said skins containing micropores invisible at 10,000 times magnification, the membranes having a sieving coefficient for passage therethrough of liquids containing solutes of a selected molecular weight range within a molecular weight range of about 5000 to 200,000 in one direction that is different than that for the passage therethrough of the same fluids in the opposite direction, the opposite ends of said enclosure being formed by a polymeric resin which envelopes the exteriors of said fibers, the opposite ends of said fibers extending through said polymeric resin, inflow means for a first fluid which is in fluid flow communication with the interiors of said membranes, outflow means in fluid flow communication with the other ends of said membranes for outflow of said first fluid, a fluid flow path comprising inflow and outflow passages in fluid flow communication with the interior of said enclosure whereby a second fluid can be caused to flow in contact with the exterior surfaces of said membranes.

13. A device according to claim 12 wherein the sieving coefficient for said molecules is greater for passage from exterior to interior of said fibers than from interior to exterior.

14. A device according to claim 12 wherein the sieving coefficient for said molecules is greater for passage from interior to exterior of said fibers than from exterior to interior.

* * * * *